United States Patent [19]  [11]  4,174,296
Kass  [45]  Nov. 13, 1979

[54] WATER SOLUBLE LECITHIN COMPOSITION

[75] Inventor: Gus S. Kass, Skokie, Ill.

[73] Assignee: American Lecithin Company, Atlanta, Ga.

[21] Appl. No.: 965,998

[22] Filed: Dec. 4, 1978

[51] Int. Cl.$^2$ ............ B01J 13/00; C11D 9/30; A23J 7/00

[52] U.S. Cl. .................... 252/312; 252/109; 252/110; 252/545; 252/354; 252/356; 424/70; 424/71; 260/403

[58] Field of Search ........... 260/403; 252/312, 354, 252/356, 109, 110, 545; 424/70, 71

[56] References Cited

U.S. PATENT DOCUMENTS

| | | | |
|---|---|---|---|
| 1,934,005 | 11/1933 | Rewald | 252/312 |
| 3,359,201 | 12/1967 | Eichberg | 252/356 |
| 3,505,074 | 4/1970 | Pardun | 252/312 |
| 3,640,880 | 2/1972 | Martin | 252/545 |
| 3,842,847 | 10/1974 | Hewitt et al. | 252/545 |
| 4,056,558 | 11/1977 | Sundby | 252/545 |

*Primary Examiner*—John F. Niebling
*Attorney, Agent, or Firm*—Jones, Thomas & Askew

[57] ABSTRACT

A method of improving the solubility of lecithin comprises steps which include the step of mixing lecithin with a solubilizing agent selected from the group consisting of tertiary amine oxides, alkyl alcohol sulfate salts, alkylamidopropyl betaines, sodium alkene sulfonates, alkyl sulfo acetates and disodium salt of monoalkyl amide of sulfosuccinate. The lecithin is rendered infinitely soluble in water and soluble in limited quantities of aqueous ethanol.

20 Claims, No Drawings

WATER SOLUBLE LECITHIN COMPOSITION

DESCRIPTION

BACKGROUND OF THE INVENTION

This invention relates to a method of improving the solubility of lecithin in water and to compositions for enhancing the utility of lecithin.

The term lecithin, in general, refers to the phospholipid or phosphatide groupd of substances which are widely distributed in nature. These are mixtures of the diglycerides of fatty acids linked to the choline ester of phosphoric acid. Commercial lecithin, derived from soybeans and containing a carrier of soybean oil, is the principal lecithin of commerce although it may also be obtained from other vegetable and animal sources, such as corn oil, safflower oil or egg yolk.

The acetone insoluble fraction of commercial soybean lecithin and of crude lecithin from other sources is a mixture of phosphatides and particularly phosphatidyl choline, phosphatidyl ethanolamine and inositol phosphatides along with glycolipids, sterol glycosides, phosphatidic acid and other polar lipids. This product, which may or may not contain a carrier of soybean oil, with its mixture of phosphatides is known in the trade as lecithin. The acetone insoluble phosphatides, substantially free of oil, may be extracted with alcohol to provide an alcohol extract which contains more phosphatidyl choline while the alcohol insoluble residue contains more phosphatidyl ethanolamine and inositol phosphatides and for the purposes of this invention lecithin and associated phosphatides substantially free of fatty oil are preferred. Lecithin is a vital constituent of all living cells where it plays a fundamental role in cell permeability and cell metabolism.

Phospholipids (more particularly choline lecithin) are reported to be an essential constituent of the natural moisturizing factor of the skin and are essential in giving the skin an attractive appearance. The phospholipids applied to the skin are at least partly resorbed by the body, as indicated by use of phospholipids tagged with radioactive iodine. Phospholipids are claimed to influence the suppleness of the skin and the elasticity of skin and hair. It softens hair, imparts sheen, improves body and reduces its electrostatic charge. It has been shown that phospholipids increase skin respiration and protects the skin against defatting by detergents. Absorption of lecithin is enhanced if the lecithin is reduced in size from large colloidal aggregates to the smaller molecular solute.

Commercial soybean lecithin, essentially free from oil, is a yellow, somewhat waxy solid that is soluble in most fat solvents and in hot fatty oils and in mineral oil lipid materials but is insoluble in water. Soaking in water will hydrate the lecithin and yield an opaque dispersion or emulsion. Its insolubility in water has limited its usefullness in skin and hair care preparations. Many products are relatively oil or fat free or contain such a low level of lipids that the amount of lecithin that can be incorporated in the product is too little to be of any significance. Prior to the present invention, lecithin has been generally used by dissolving the lecithin in the fatty or lipid portion of oil-water systems. If such systems were relatively free of the lipid materials that served as solvents for lecithin, the lecithin was included in the system as a dispersion or emulsion which was often unstable, of limited effectiveness or incompatible with other components.

SUMMARY OF THE INVENTION

The present invention is a simple direct method of preparing clear or translucent, stable aqueous solutions of lecithin. The method combines lecithin with tertiary amine oxides, or with one of the preferred surfactants such as alkyl alcohol sulfate salts, alkylomidopropyl betaine, disodium salt of monoalkyl amide of sulfosuccinate, alkyl sulfo acetates or sodium alkene sulfonates to effect a surprising solubilizing action at ambient or room temperatures. The tertiary amine oxides and surfactants function as solubilizing agents. A first method, in accordance with the invention, includes steps of mixing lecithin with water until the lecithin is thoroughly hydrated creating an opaque dispersion that is free of lumps; then, an aqueous solution of one of the solubilizing agents is added to the dispersion at a prefixed ratio of solubilizing agent to lecithin. A second method, in accordance with the present invention, includes steps of mixing solid lecithin with an aqueous solution of one of the solubilizing agents until the lecithin goes into solution forming a concentrate; then, the concentrate is introduced into water or water based systems.

Therefore, it is an object of this invention to provide a unique method of incorporating lecithin into skin and hair care products and in other products with water-containing systems.

Another object of this invention is to provide a novel surfactant composition wherein lecithin is immediately dissolved in a water phase of an emulsion instead of in an oil phase.

Yet another object of this invention is to provide a novel water soluble concentrate of lecithin and amine oxide or specific surfactants that yields infinitely dilutable water solutions that remain clear or relatively clear and stable.

Still another object of this invention is to provide a water soluble concentrate of lecithin for the easy addition of lecithin to water based cosmetics or toiletries.

Another object of this invention is to provide lecithin and related phosphatides in a water system in a solubilized form.

Other objects, features and advantages of the present invention will become apparent upon reading the following specification.

DESCRIPTION OF THE PREFERRED EMBODIMENTS

The present invention relates to a unique use of tertiary amine oxides, or surfactants as a solubilizer (or solubilizing agent) to either render lecithin and associated phosphatides soluble in water or to exert a remarkable solubilizing effect whereby aqueous systems of much greater clarity or substantial transparency are obtained. It has been found that amine oxides corresponding to the following general chemical structures are effective lecithin solubilizers:

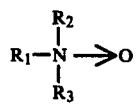

(Formula 1)

in which $R_1$ is an alkyl chain of 8–18 carbons and $R_2$ and $R_3$ represent methyl, ethyl or hydroxy ethyl groups.

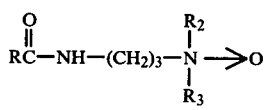

(Formula 2)

in which

represents the coconut or tallow fatty acid radical.

The amine oxides listed below are particular examples of suitable oxides when used either singly or in mixture:
Lauryldimethylamine oxide
Cocodimethylamine oxide
Myristyldimethylamine oxide
Cetyldimethylamine oxide
Oleyldimethylamine oxide
Cocamidopropyldimethylamine oxide
Tallowamidopropyldimethylamine oxide Soybean lecithin with or without naturally associated phosphatides, as well as lecithin derived from egg yolk and other sources can be solubilized in accordance with the present invented method. The soybean lecithin is substantially insoluble in acetone and contains not more than a relatively small amount of triglyceride. An example of this type lecithin is the phosphatides obtained from crude commercial oil containing lecithin by acetone extraction. The water solubilized lecithin is not adversely affected by the presence of minor amounts oil or fat (triglyceride) in the system.

Lecithin has likewise been found to possess remarkably improved solubility in aqueous systems in combination with many of the most popular surfactants utilized in the making of shampoos including alkyl alcohol sulfate salts, alkylamidopropyl betaine, sodium alkene sulfonates, alkyl sulfoacetates and disodium salt of monoalkyl amide of sulfosuccinate.

Alkyl alcohol sulfate salts corresponding to the following general formula are effective solubilizers (or solubilizing agents):

R —OSO$_3$—X in which R may be lauryl, cetyl, decyl, tallow, oleyl tridecyl or myristyl. X may be sodium, potassium, magnesium, ammonium, triethanolamine, diethanolamine or monoethanolamine. For example, typical of the lauryl sulfate salt group of alkyl alcohol sulfate salts is sodium lauryl sulfate having the following formula:

$CH_3—(CH_2)_{10}—CH_2—OSO_3—Na$

Disodium salt of monoalkyl amide of sulfosuccinate conforming generally to the following formula are effective solubilizers:

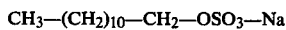

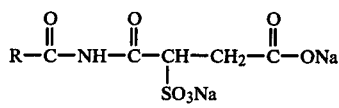

where

R—C— may be lauric, myristic, oleic, linoleic, palmitic, tallow or coconut fatty acid radicle or ethoxylated fatty acid radical. An example is disodium monooleamido sulfosuccinate in which the

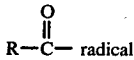

R—C— radical has the following structure:

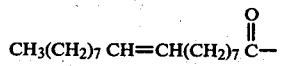

$CH_3(CH_2)_7\ CH=CH(CH_2)_7\ C—$

Alkylamidopropyl betaine that conforms generally to the following formula is likewise an effective solubilizer:

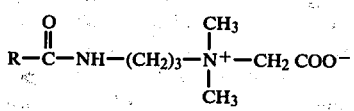

where

R—C— may be a fatty acid radical (the same as shown above). An example is cocamidopropyl betaine in which R represents the coconut fatty acid radical.

Sodium alkene sulfonates conforming generally to the following formula have likewise been found to be effective solubilizers:

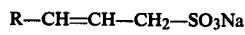

$R—CH=CH—CH_2—SO_3Na$ where R represents the $C_{12}-C_{18}$ hydrocarbon group. An example is sodium alpha olefin sulfonate in which R represents a mixture of $C_{14-16}$ hydrocarbons.

The lecithin can be conveniently solubilized by the method of the present invention as described below. In a preferred method, lecithin is first soaked in water, with or without stirring, until the lecithin is thoroughly hydrated and the opaque dispersion is free of lumps. An aqueous solution of a selected solubilizer, for example amine oxide is then added to the dispersion, at a prefixed ratio of active amine oxide to lecithin. This may be done at room temperature (15°-30° C.) or may be done with warming. The mixture is then stirred resulting in a clear and transparent liquid as the lecithin rapidly goes into solution. The mixture may be warmed to reduce the viscosity of some amine oxides that are marketed in the form of viscous pastes or gels. The speed of solution usually varies from several seconds to two minutes.

The same procedure may be used to dissolve lecithin in solutions of the listed popular shampoo surfactants including those described above. However, solubility in these solutions is speeded by the addition of heat (50°-60° C.).

An alternate method of preparing a clear, stable solution of lecithin is to mix the solid lecithin with commercially available aqueous solutions of the solubilizers defined above without the addition of water or other solvent or with a minimum amount of water to form a concentrate solution. Complete solution of the lecithin will require from about two to twenty-four hours. The concentrate solutions of lecithin and solubilizer prepared during the course of this alternate method offer a convenient method of introducing lecithin into water based systems, as into the water phase of a cosmetic emulsion.

As regards the use of amine oxides as solubilizers, the ratio of amine oxide to lecithin will vary from one to two parts of amine oxide or more to one part of lecithin. This variation is dependent upon the amine oxide used and the character of the lecithin product used. Commercial amine oxides are supplied as aqueous or alcoholic concentrates containing from 25–40% of amine oxide. Aqueous amine oxide solutions are preferred to the alcohol solutions. There is a minimum ratio of 100% amine oxide to lecithin to achieve solubility or optimum clarity. For example, if 100 grams of a 40% amine oxide concentrate will solubilize 20 grams of lecithin, the ratio is two parts of amine oxide to one part of lecithin. The various amine oxides may have different solubilization affects on the same lecithin. Since they differ in molecular size and structure, the amine oxides also differ in the ratio of amine oxide to lecithin to obtain solubility. It has been found that there are often slight differences from lot to lot of the same grade of lecithin from a supplier. This may be due to variable residual amounts of acetone soluble lipids. The same amine oxide that will solubilize lecithin of a particular lot may solubilize lecithin of another lot but at a higher or lower ratio of amine oxide to lecithin. The selection of the preferred amine oxide will depend upon the compositions and end use of the product.

In evaluating the solubility properties of the concentrate solutions of lecithin (phosphatides) and alkyl alcohol sulfate salts as prepared by the alternate method above, a dilution of 10% of the concentrate solution and 90% distilled water is prepared for a number of concentrate solutions with the following results:

| Conc. Solution No. | Alkyl Alcohol Sulfate Salt | % Soybean Lecithin | Ratio | Appearance of the Dilution |
|---|---|---|---|---|
| 5180(a) | SLS | 15 | 1.4/1 | clear |
| 5222 | ALS | 12 | 2/1 | clear |
| 5228 | TLS | 12 | 1.4/1 | clear |
| 5230 | TLS | 12 | 2/1 | clear |

The concentrate solutions associated with each concentrate solution number above are compositions of lecithin and an alkyl alcohol sulfate salt identified as follows:
SLS: Sodium lauryl sulfate
ALS: Ammonium lauryl sulfate
TLS: Triethanolamine lauryl sulfate Concentrate solution 5180(a) is a composition of 21.5 parts lecithin, 21.8 parts water, and 100 parts of 30% active sodium lauryl sulfate.

Concentrate solution 5222 is a composition of 30 parts lecithin, 20 parts water, and 200 parts of 30% active ammonium lauryl sulfate.

Concentrate solution 5228 is a composition of 30 parts lecithin, 115 parts water and 105 parts of 40% active triethanolamine lauryl sulfate.

Concentrate solution 5230 is a composition of 30 parts lecithin, 50 parts water and 150 parts of 40% active triethanolamine lauryl sulfate.

The ratios are all based on active basis. Under the heading "Ratio" in the above table, the first number is the alkyl alcohol sulfate salt and the second number is the lecithin (acetone insoluble phosphatides). At the given ratios, the dilutions shown are infinitely soluble in water. The dilution prepared from Concentrate No. 5228 for example is a crystal clear, golden colored liquid of moderate viscosity. The dilution has a relatively low ratio of alkyl alcohol sulfate salt (TLS) to lecithin (1.4/1), with good solubility in aqueous alcohol (as explained below).

The lauryl sulfates are supplied in commerce as concentrated aqueous solutions in which the surfactant salt itself will vary from 28–60%. Some salts are also supplied as granular or powder solids with an activity of 96% or better.

The concentrate solutions described above that are clearly water soluble are also miscible with ethanol up to a maximum of about 40%. As a further check on solubility in ethanol, an unexpected finding since the acetone insoluble soybean phosphatides are only very slightly soluble in ethanol, a 20% dilution of the concentrate solutions was prepared and then ethanol was added until turbidity resulted. This established an upper limit of ethanol and the addition of ethanol below this level yields a clear solution. Solutions of the following composition were prepared:

| From Conc. Solution 5180(a) | |
|---|---|
| Lecithin | 2.00% |
| SLS | 1.82 |
| Ethanol | 35.00 |
| Water | 61.18 |
| From Conc. Solution 5222 | |
| Lecithin | 1.30% |
| ALS | 2.60 |
| Ethanol | 46.00 |
| Water | 50.10 |
| From Conc. Solution 5228 | |
| Lecithin | 1.37% |
| TLS | 1.92 |
| Ethanol | 42.80 |
| Water | 53.91 |
| From Conc. Solution 5230 | |
| Lecithin | 1.30% |
| TLS | 2.60 |
| Ethanol | 46.00 |
| Water | 50.10 |

The percent alcohol is by volume. All of the above solutions were crystal clear. If higher levels of alcohol are added, hazy or turbid liquids result.

By using concentrates developed in accordance with the present method, it is now possible to incorporate up to 2.0% of lecithin in aqueous alcohol systems containing up to 46% of alcohol. This is not possible when lecithin is used alone.

Whereas greatest attention has been given to the amine oxides and the lauryl sulfates, the breadth of the present invention is not intended to be limited thereto as the other surfactants described above are considered to be equally important in view of the inventive concept disclosed herein. There exists for each of the subject surfactants a minimum ratio, as with the alkyl alcohol sulfate salts described above, of surfactant to lecithin below which there is no solubility. That is, there is a minimum amount of solubilizer (surfactant or amine oxide) which will solubilize a given amount of lecithin to form a clear solution in water.

The following examples are illustrative of the present invention, and while they cover specific embodiments of the present invention, it will be readily apparent to one skilled in the art that these are given merely by way of explanation, not of limitation, and that numerous changes in the details may be made without departing from the spirit and scope of the invention as hereinafter claimed. The lecithin granules comprise soybean phosphatides 95% insoluble in acetone.

All parts given are by weight unless otherwise stated. Although any consistent unit of weight could be employed, the weights of the following examples are given in grams.

EXAMPLE 1

The ingredients of this first example are as follows:

| Lecithin, granules | 25.0 |
|---|---|
| Cocodimethylamine oxide (30% soln.) | 100.0 |
| Water | 31.0 |

The above ingredients are mixed and, after several hours, the mixture forms a clear, viscous liquid that yields a clear solution when diluted with water. This mixture (prior to dilution) contains 19.2% of amine oxide and 16% of lecithin.

EXAMPLE 2

The ingredients of Example 2 are the same as Example 1. The lecithin is first hydrated with the water for two hours and then the amine oxide is added. A clear solution results in one minute; much more rapidly than in Example 1.

EXAMPLE 3

The ingredients of this third example are as follows:

| Lecithin granules | 21.5 |
|---|---|
| Water | 21.8 |
| Lauryldimethylamine oxide (30% soln) | 100.0 |

The lecithin is first hydrated with the water for one hour. Upon stirring in the amine oxide, a clear, viscous, amber liquid results that forms a clear water solution upon dilution. The resulting liquid (before dilution) contains 20.9% amine oxide and 15.0% lecithin.

EXAMPLE 4

The ingredients of Example 4 are as follows:

| Lecithin granules | 28.66 |
|---|---|
| Water | 14.64 |
| Lauryldimethylamine oxide (40% soln) | 100.0 |

The lecithin is first hydrated with the water for one hour. Upon stirring in the amine oxide a clear, viscous, amber liquid results that forms a clear water solution upon dilution with water. The resulting liquid (before dilution) contains 28% of amine oxide and 20% of lecithin.

EXAMPLE 5

The ingredients of Example 5 are as follows:

| Lecithin granules | 17.9 |
|---|---|
| Water | 20.1 |
| Tallowamidopropyldimethylamine oxide (25% soln.) | 100.0 |

A mixture comprising the above ingredients is stirred while heating in a hot water bath at 60° C. The mixture forms a clear, amber colored liquid that yields a clear solution upon dilution with water. The mixture (prior to dilution) contains 13% lecithin and 18.1% amine oxide.

EXAMPLE 6

The ingredients of Example 6 are as follows:

| Lecithin granules | 10.0 |
|---|---|
| Water | 90.0 |
| Cocamidopropyldimethylamine oxide (30% soln.) | 43.5 |

The lecithin is hydrated with the water for one hour and then the amine oxide is added. A clear liquid quickly results that yields a clear solution upon dilution with water. A dilution containing 2% lecithin remains clear after two freeze/thaw cycles. The concentrate (resulting liquid prior to dilution) contains 7% lecithin and 9% amine oxide.

EXAMPLE 7

The ingredients of Example 7 are as follows:

| Lecithin Granules | 10.0 |
|---|---|
| Water | 90.0 |
| Cetyldimethylamine oxide (30% soln.) | 50.0 |

A mixture of the above ingredients is stirred and heated to 50° C. A clear, viscous concentrated liquid results that contains 6.66% lecithin and 10.0% amine oxide. When 30 parts of the concentrate, containing 2% lecithin, is diluted with 70 parts of water, a clear viscous solution results.

EXAMPLE 8

The following ingredients are used in Example 8 to produce an Antiperspirant Lotion:

| Lecithin/amine oxide concentrate as shown in Example 6 | 14.3 |
|---|---|
| Water | 41.2 |
| Glycerol monostearate | 3.0 |
| PEG-50 Stearate | 0.5 |
| Methylparaben | 0.2 |
| Aluminum Chlorohydrate (50% soln.) | 40.0 |

The fatty components of glycerol monostearate and PEG-50 stearate, at 70° C., are added while stirring, to a solution including the water, methylparaben and lecithin/amine oxide concentrate at 70° C. The resulting amulsion is cooled to 50° C. and the aluminum chlorohydrate added. The resulting cream colored lotion contains 1% lecithin.

EXAMPLE 9

The ingredients of Example 9 yield a liquid hair conditioner:

| | |
|---|---|
| Lecithin/amine oxide concentrate as shown in Example 6 | 14.3 |
| Water | 69.6 |
| Natrosol 250HHR | 0.4 |
| Water | 13.5 |
| Cetyl trimethyl ammonium chloride (50% soln.) | 2.0 |

The natrosol is dissolved in the water at 60° C. The other ingredients are then added. Sufficient citric acid is added to adjust the pH to 4.0–4.5, which is a desirable pH for a hair conditioner. The resulting solution is a crystal clear liquid hair conditioner with a viscosity of 300–400 cps.

EXAMPLE 10

The ingredients of Example 10 are as follows:

| | |
|---|---|
| Lecithin Granules | 18.00 |
| Cocamidopropyldimethylamine oxide | 77.14 |
| Water | 4.86 |

A mixture of the above ingredients is stirred for one hour and then allowed to stand for 24 hours, after which the mixture is again stirred for one hour. A viscous, amber colored clear gel results which is soluble in water. 5.555 grams of the clear gel concentrate contains 1.0 gram of lecithin.

EXAMPLE 11

Hard milled soap bars are prepared from 94.445 parts of soap and 5.555 parts of the clear gel, lecithin concentrate shown in Example 10. Each bar contains 1.0% of lecithin. These bars, when tested against control bars without lecithin, diminish the defatting action of the soap on the skin.

EXAMPLE 12

The following ingredients are used in Example 12 to produce a shampoo:

| | |
|---|---|
| Water | 50.0 |
| Ammonium Lauryl Sulfate, (30% soln.) | 29.0 |
| Lecithin concentrate No. 5222 | 4.0 |
| Ammonium Lauryl Ether Sulfate, (60% soln.) | 11.0 |
| Cocamide-DEA | 1.0 |
| Preservative, fragrance, color | q.s. |
| Water to make | 100.0 |

The ammonium lauryl sulfate is dissolved in the water at 60° C. and then the other ingredients are added in the order shown. The resulting shampoo is crystal clear with moderate viscosity.

EXAMPLE 13

The following ingredients are used in Example 13 to produce a shampoo:

| | |
|---|---|
| Water | 64.0 |
| Triethanolamine Lauryl Sulfate, 40% | 28.0 |
| Lecithin concentrate No. 5230 | 3.0 |
| Cocamide-DEA | 3.0 |
| Preservative, fragrance, color | q.s. |
| Water to make | 100.0 |

The ingredients are dissolved in the water at approximately 20° C. A crystal clear shampoo results with good foaming qualities.

EXAMPLE 14

The following ingredients are used in Example 14 to produce Shampoo:

| | |
|---|---|
| Water | 60.00 |
| Sodium Lauryl Sulfate, 28% | 20.2 |
| Lecithin concentrate No. 5180(a) | 4.8 |
| Cocamide-DEA | 4.0 |
| Ethylene Glycol Monostearate | 1.0 |
| Sodium Chloride | 1.0 |
| Water to make | 100.0 |

The water is heated to 60° C. and each ingredient dissolved in the order shown. Sufficient citric acid is added to adjust the pH to 7.5 which is a desirable pH for a shampoo. The resulting pearly lotion shampoo contains 2% of lecithin.

EXAMPLE 15

The following ingredients are used in Example 15 to produce a Bubble Bath:

| | |
|---|---|
| Water | 51.0 |
| Alpha Olefin Sulfonate, sodium, 39% | 30.0 |
| Lecithin concentrate No. 5230 | 6.0 |
| Sodium Lauryl Ether Sulfate, 30% | 9.0 |
| Cocamide-DEA | 4.0 |

The ingredients are dissolved in the water at 50° C. This clear, liquid bubble bath contains 2% of lecithin.

EXAMPLE 16

The following ingredients are used in Example 16 to produce a clear shampoo:

| | |
|---|---|
| Water | 52% |
| Cocoamidopropyl betaine | 10% |
| Lecithin granules | 2% |
| Sodium lauryl ether sulfate (60%) | 34% |
| preservative, fragrance, color q.s. | |
| Water to make | 100% |

Dissolve the cocoamidopropyl betaine in the water and heat at 60° C. Add the lecithin and stir until solution is complete. Then add the other ingredients in the order shown. This is a clear very viscous shampoo.

EXAMPLE 17

The following ingredients are used in Example 17 to produce a clear shampoo:

| | |
|---|---|
| Water | 40% |
| Sulfosuccinate of oleyl monoethanolamide | 40% |
| Lecithin powder | 1% |
| Cocamide-DEA | 2% |
| Sodium lauryl ether sulfate (60% soln.) | 10% |

| -continued | |
|---|---|
| Water to make | 100% |

The water and sulfosuccinate are heated to 60° C. The lecithin is then added and the mixture stirred until solution is complete. The other ingredients are then added. A clear shampoo results.

EXAMPLE 18

Four (4) parts lecithin granules are mixed directly with 16 parts 30% active sodium lauryl sulfate and the composition is warmed and stirred. The lecithin is completely dissolved resulting in a clear liquid which is infinitely soluble in water.

EXAMPLE 19

Three (3) parts lecithin granules are mixed directly with 25 parts 28–30% active ammonium lauryl sulfate and the composition is warmed and stirred. The lecithin is completely dissolved resulting in a clear liquid which is infinitely soluble in water.

EXAMPLE 20

Three (3) parts lecithin granules are mixed directly with 25 parts 25–40% cocodimethylamine oxide and the composition is warmed and stirred. The lecithin is completely dissolved resulting in a clear liquid which is infinitely soluble in water.

While this invention has been described in specific detail with particular reference to preferred embodiments thereof, it will be understood that variations and modifications can be effected within the spirit and scope of the invention as described hereinbefore and as defined in the appended claims.

I claim:

1. Method of increasing the solubility of lecithin, said method comprising the step of adding to an aqueous dispersion of lecithin an amount of solubilizing agent sufficient to solubilize the lecithin, said solubilizing agent selected from the group consisting of tertiary amine oxides, alkyl alcohol sulfate salts, alkylamidopropyl betaines, sodium alkene sulfonates, alkyl sulfo acetates and disodium salt of monoalkyl amide of sulfosuccinate.

2. Method of increasing the water solubility of lecithin, said method comprising the step of combining lecithin with an amount of solubilizing agent sufficient to render the lecithin water soluble, said solubilizing agent selected from the group consisting of tertiary amine oxides, alkyl alcohol sulfate salts, alkylamidopropyl betaines, sodium alkene sulfonates, alkyl sulfo acetates and disodium salt of monoalkyl amide of sulfosuccinate.

3. Method of claim 1 or 2, wherein said tertiary amine oxide has the structure:

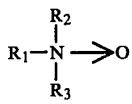

wherein $R_1$ is an alkyl group of 8–18 carbons and $R_2$ and $R_3$ are either methyl, ethyl or hydroxy ethyl.

4. Method of claim 1 or 2, wherein said tertiary amine has the structure:

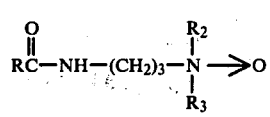

wherein

is either a coconut oil fatty acid radical or a tallow fatty acid radical and $R_2$ and $R_3$ are either a methyl, an ethyl or a hydroxy ethyl group.

5. Method of claim 1 or 2, wherein said tertiary amine oxide is selected from the group consisting of Lauryldimethylamine oxide, Cocodimethylamine oxide, Myristyldimethylamine oxide, Cetyldimethylamine oxide, Oleyldimethylamine oxide, Cocamidopropyldimethylamine oxide, and Tallowamidopropyldimethylamine oxide.

6. Method of claim 1 or 2 wherein the alkyl alcohol sulfate salt has the structure:

R—OSO₃—X wherein R is lauryl, cetyl, decyl, tallow, tridecyl, oleyl or myristyl and X is sodium, potassium, magnesium, ammonium, triethanolamine, diethanolamine or monoethanolamine.

7. Method of claim 1 or 2, wherein the disodium monoalkyl amide of sulfosuccinate has the structure:

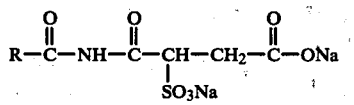

wherein

is a lauric, myristic, oleic, linoleic, palmitic, tallow, coconut or ethoxylated fatty acid radical.

8. Method of claim 1 or 2, wherein the alkylamidopropyl betaine has the formula

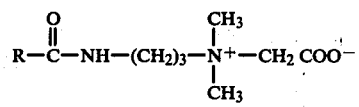

wherein

is a lauric, myristic, oleic, linoleic, palmitic, tallow, coconut or ethoxylated fatty acid radical.

9. Method of claim 1 or 2, wherein the sodium alkene sulfonate has the formula

R—CH=CH—CH₂—SO₃Na where R is taken from the $C_{12}$–$C_{18}$ hydrocarbon group.

10. A clear aqueous solubilized liquid comprising:
water;
lecithin; and
a solubilizing agent selected from the group consisting of tertiary amine oxides, alkyl alcohol sulfate salts, alkylamidopropyl betaines, sodium alkene sulfonates, alkyl sulfo acetates and disodium salt of monoalkyl amide of sulfosuccinate.

11. A clear aqueous solubilized liquid comprising:
water;
lecithin, normally insoluble in said water; and
a solublizing agent in a quantity sufficient to render the liquid composition clear,
said solubilizing agent selected from the group consisting of tertiary amine oxides, alkyl alcohol sulfate salts, alkylamidopropyl betaines, sodium alkene sulfonates, alkyl sulfo acetates and disodium salt of monoalkyl amide of sulfosuccinate;
said lecithin being solubilized in said water by the addition of said surfactant.

12. The liquid of claim 11 further comprising ethanol.

13. The liquid of claim 11 wherein the ratio by weight of said solubilizing agent to said lecithin is greater than or equal to approximately 1:1.

14. The liquid of claim 11 wherein said tertiary amine oxides have the structure:

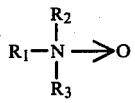

wherein $R_1$ is an alkyl group of 8–18 carbons and $R_2$ and $R_3$ are either methyl, ethyl or hydroxy ethyl groups.

15. The liquid of claim 11 wherein said tertiary amine oxides have the structure:

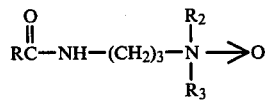

wherein

is either a coconut oil fatty acid radical or a tallow fatty acid radical and $R_2$ and $R_3$ are either a methyl, an ethyl or a hydroxy ethyl group.

16. The liquid of claim 11 wherein said tertiary amine oxide is selected from the group consisting of Lauryldimethylamine oxide, Cocodimethylamine oxide, Myristyldimethylamine oxide, Cetyldimethylamine oxide, Oleyldimethylamine oxide, Cocamidopropyldimethylamine oxide, and Tallowamidopropyldimethylamine oxide.

17. The composition of claim 11 wherein said alkyl alcohol sulfate salt has the structure:

wherein R is lauryl, cetyl, decyl, tallow, tridecyl, oleyl or myristyl and is sodium potassium, magnesium, ammonium, triethanolamine, diethanolamine or monoethanolamine.

18. The liquid of claim 11 wherein said disodium monoalkyl amide of sulfosuccinate has the structure:

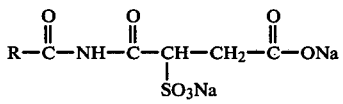

where

is a lauric, myristic, oleic, linoleic, palmitic, tallow, coconut or ethoxylated fatty acid radical.

19. The liquid of claim 11 wherein said alkylamidopropyl betaine has the structure:

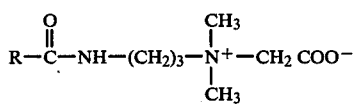

where

is a lauric, myristic, oleic, linoleic, palmitic, tallow, coconut or ethoxylated fatty acid radical.

20. The liquid of claim 11 wherein said sodium alkene sulfonate has the structure:

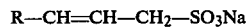

where R is taken from the $C_{12}$–$C_{18}$ hydrocarbon group.

* * * * *